(12) United States Patent
Schmitt et al.

(10) Patent No.: US 9,300,936 B2
(45) Date of Patent: Mar. 29, 2016

(54) CAMERA ARRANGEMENT FOR IMAGE DETECTION, X-RAY SYSTEM AND METHOD FOR BALANCING AND OPERATING

(71) Applicant: FRAUNHOFER-GESELLSCHAFT ZUR FOERDERUNG DER ANGEWANDTEN FORSCHUNG E.V., Munich (DE)

(72) Inventors: Peter Schmitt, Erlangen (DE); Guenther Kostka, Erlangen (DE); Rolf Behrendt, Dormitz (DE); Andreas Jobst, Nuremberg (DE); Matthias Kube, Fuerth (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 26 days.

(21) Appl. No.: 14/176,028

(22) Filed: Feb. 7, 2014

(65) Prior Publication Data
US 2014/0219414 A1 Aug. 7, 2014

Related U.S. Application Data

(63) Continuation of application No. PCT/EP2012/065700, filed on Aug. 10, 2012.

(60) Provisional application No. 61/523,109, filed on Aug. 12, 2011.

(51) Int. Cl.
*H04N 9/73* (2006.01)
*A61B 6/00* (2006.01)
(Continued)

(52) U.S. Cl.
CPC ............. *H04N 9/735* (2013.01); *A61B 6/5258* (2013.01); *G01N 23/046* (2013.01); *H04N 5/32* (2013.01); *H04N 5/3653* (2013.01); *G06T 5/002* (2013.01)

(58) Field of Classification Search
CPC ........ A61B 6/52; A61B 6/5258; G01N 23/00; G01N 23/02; G01N 23/04; G01N 23/046; G06T 5/00; G06T 5/001; G06T 5/002; H04N 5/00; H04N 5/04; H04N 5/045; H04N 5/30; H04N 5/32; H04N 5/335; H04N 5/357; H04N 5/365; H04N 5/3651; H04N 5/3653
USPC ........... 378/4, 21, 62, 91, 98, 98.7, 98.8, 204; 378/210, 901; 382/128, 131, 168, 169; 348/222.1, 241, 251, 607, 615
See application file for complete search history.

(56) References Cited

U.S. PATENT DOCUMENTS 3,621,129 A 11/1971 Fisher
3,800,078 A 3/1974 Cochran et al.
(Continued)

FOREIGN PATENT DOCUMENTS

DE 102009032441 1/2011

*Primary Examiner* — Anastasia Midkiff
(74) *Attorney, Agent, or Firm* — Michael A. Glenn; Perkins Coie LLP

(57) ABSTRACT

A camera arrangement for image detection includes radiation-sensitive sensor elements arranged to record a common object plane in offset fields of view, a balancer and a shading corrector. The balancer is implemented, for balancing the sensor elements, to post-process for each sensor element a sensor signal of the respective sensor signal n by means of balancing information determined in balancing and stored, so that a variation of the intensity I of incoming radiation in the respective field of view leads to a change of the respective post-processed sensor signal according to a desired mapping function $F_n(a_n I)$, the mapping functions $F_n( )$ of all factory-balanced sensor elements being identical, and $a_n$ being a sensor-individual factor. The shading corrector is implemented on the basis of a recording generated by means of the camera arrangement with the sensor elements, to change the sensor element-individual factors $a_n$ so that intensity differences of the recording are balanced across the common object plane.

27 Claims, 7 Drawing Sheets

(51) Int. Cl.
*H04N 5/32* (2006.01)
*H04N 5/365* (2011.01)
*G01N 23/04* (2006.01)
*G06T 5/00* (2006.01)

(56) References Cited

U.S. PATENT DOCUMENTS

| | | |
|---|---|---|
| 3,979,555 A | 9/1976 | Opittek et al. |
| 4,232,400 A | 11/1980 | Yamamoto et al. |
| 4,493,106 A | 1/1985 | Farhangi et al. |
| 4,504,864 A | 3/1985 | Anastassiou et al. |
| 4,504,972 A | 3/1985 | Scherl et al. |
| 4,578,712 A | 3/1986 | Matsunawa |
| 4,695,884 A * | 9/1987 | Anastassiou et al. ......... 348/615 |
| 6,072,603 A | 6/2000 | Parks |
| 2002/0021786 A1 | 2/2002 | Hamamoto |
| 2003/0234866 A1 | 12/2003 | Cutler |
| 2007/0008413 A1 | 1/2007 | Meisenzahl et al. |
| 2008/0151079 A1 | 6/2008 | Iijima et al. |

* cited by examiner

| $I_{1,2,3,4}$ | pixel 1 | pixel 2 | pixel 3 | pixel 4 | ⌀ |
|---|---|---|---|---|---|
| 0W | $AW_1$ : 0,5 ⇒ 0<br>$F_1$ : 0<br>$G_1$ : 0 | $AW_2$ : 0<br>$F_2$ : 0<br>$G_2$ : 0 | $AW_3$ : 0<br>$F_3$ : 0<br>$G_3$ : 0 | $AW_4$ : 0<br>$F_4$ : 0<br>$G_4$ : 0 | 0 |
| 1W | $AW_1$ : 1,5 ⇒ 1<br>$F_1$ : 1<br>$G_1$ : 1,5 | $AW_2$ : 1<br>$F_2$ : 1<br>$G_2$ : 0,75 | $AW_3$ : 2<br>$F_3$ : 1<br>$G_3$ : 0,75 | $AW_4$ : 2<br>$F_4$ : 1<br>$G_4$ : 1,5 | |
| 2W | $AW_1$ : 2,5 ⇒ 2<br>$F_1$ : 2<br>$G_1$ : 3 | $AW_2$ : 1,5<br>$F_2$ : 2<br>$G_2$ : 1,5 | $AW_3$ : 4<br>$F_3$ : 2<br>$G_3$ : 1,5 | $AW_4$ : 4<br>$F_4$ : 2<br>$G_4$ : 3 | 1,5 |
| 3W | $AW_1$ : 3,5 ⇒ 3<br>$F_1$ : 3<br>$G_1$ : 4,5 | $AW_2$ : 2,5<br>$F_2$ : 3<br>$G_2$ : 2,25 | $AW_3$ : 5<br>$F_3$ : 3<br>$G_3$ : 2,25 | $AW_4$ : 5<br>$F_4$ : 3<br>$G_4$ : 4,5 | |
| 4W | $AW_1$ : 4,0 ⇒ 3,5<br>$F_1$ : 4<br>$G_1$ : 6 | $AW_2$ : 3,5<br>$F_2$ : 4<br>$G_2$ : 3 | $AW_3$ : 6<br>$F_3$ : 4<br>$G_3$ : 3 | $AW_4$ : 6<br>$F_4$ : 4<br>$G_4$ : 6 | | illumination strength for 2W

FIG 3B

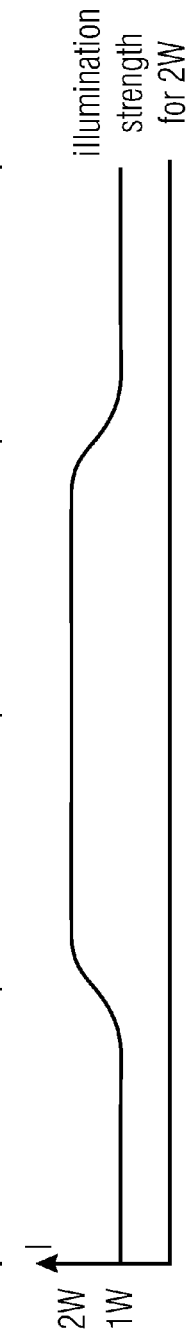

CAMERA ARRANGEMENT FOR IMAGE DETECTION, X-RAY SYSTEM AND METHOD FOR BALANCING AND OPERATING

CROSS-REFERENCE TO RELATED APPLICATIONS

This application is a continuation of copending International Application No. PCT/EP2012/065700, filed Aug. 10, 2012, which is incorporated herein by reference in its entirety, and additionally claims priority from U.S. Application No. 61/523,109, filed Aug. 12, 2011, which is also incorporated herein by reference in its entirety.

Embodiments of the present invention relate to a camera arrangement for image detection and to an x-ray system for x-ray image detection. Further embodiments relate to a method for balancing the camera arrangement or a (multi module) (x-ray) camera and for operating the same and to a computer program.

BACKGROUND OF THE INVENTION

Technical fields of application of the embodiments described here are in particular radiation-sensitive cameras as they are used in transmission systems or x-ray or computer tomography systems. Examples for this are so-called "flat-panel converters", wherein radiation is converted into visible light via an x-ray sensitive scintillator screen, so that this light may be detected by means of a camera which operates in the visible range. Typically, this visible light is detected via an extensive light-sensitive matrix detector or a camera arrangement having one or several cameras and is converted into an electronic signal.

Such cameras which are used generally show a "non-linear" or generally different performance which may differ from pixel to pixel. The consequence is that the increase of the measurement signal or increase of the brightness of the image is not uniform with respect to the increase of the illumination strength or the illumination intensity. Additionally, the sensitivity and the dark signal of each pixel or each camera may be different. This different performance is for example disturbing when the thickness of the object is to be concluded from the brightness in an x-ray recording. In particular, this has a negative influence when using a plurality of electronic cameras. Here, by each camera a partial image of the x-ray sensitive screen, which is to be optically imaged, is detected and later combined into a homogenous overall image. When combining the partial images, due to the different performances of individual pixels and/or the different sensitivities of the individual cameras clear brightness leaps may be detected at the borders. As larger flat panel converters generally are combined from several modules or camera modules or matrix detectors, the described method is to be observed in particular here.

In order to compensate for this performance, typically balancing recordings are generated at different illumination strengths. By this, the individual partial images (x-ray recordings) may be factory-balanced with respect to a different performance and with respect to the different sensitivity or the different dark signal of the individual pixels and/or cameras or modules, so that a homogenous overall image may be output. The stronger the different the characteristics are, the more balancing recordings may be used with different brightnesses or intensities in order to generate a similar (e.g. linear) output signal. For x-ray cameras put together from several individual cameras or generally several modules, this means that further with increasing deviations (non-linearity) of the individual cameras or modules an increasing number of balancing recordings with different radiation intensities is useful as otherwise the boundaries of the individual images are clearly obvious in the combined recordings and thus no homogenous image may result.

It is further enabled by this method for inhomogeneities of the radiation source to be balanced via the lateral dimensions of the x-ray recording. Such a balancing is only valid for a positioning of the (inhomogeneous) radiation source or for a distance between x-ray source and x-ray camera and for a fixed set of x-ray parameters, like e.g. x-ray voltage or illumination time. Vice versa this means, if the x-ray camera is positioned in a different location or in a different distance in the inhomogeneous radiation field or if other x-ray parameters are changed, the balancing of the x-ray camera and in particular all balancing recordings have to be regenerated.

In particular with parallel computer tomography systems or with robot computer tomography systems, frequently a plurality of balancing recording that may be used. For example with robot computer tomography systems in which by means of the first robot the x-ray source is positioned and by means of the second robot the x-ray camera, so that the object to be screened is located between the x-ray source and the x-ray camera or more accurately in the x-ray cone of the x-ray source and the x-ray camera. The first and second robots are thus each moved on predefined motion tracks, so that the object to be screened may be screened or x-rayed from different angles or different positions.

As such objects to be screened or x-rayed typically comprise varying exterior dimensions, the motion tracks of the two robots are typically not parallel. Consequently, also the distance between the radiation source and the x-ray camera varies so that the camera arrangement has to be balanced again for each x-ray recording at each x-ray position. Typically, this balancing is executed before the actual recording by the two robots arms driving along the motion tracks beforehand and detecting for example ten balancing recordings for each position. A rewritten computer tomography system drives to a plurality of for example 100 or 500 positions in one recording. Based on this, for a computer tomography recording 1000 or 5000 balancing recordings ought to be determined. In the everyday operation of such a (radiation sensitive) camera or such a computer tomography system this leads to a substantial effort. Thus, there is a need for an improved approach.

SUMMARY

According to an embodiment, a camera arrangement for image detection including a plurality of radiation-sensitive sensor elements arranged in order to record a common object plane in offset fields of view may have: a balancer implemented, for balancing the sensor elements, to post-process for each sensor element a sensor signal of the respective sensor elements n by means of balancing information determined in balancing and stored, so that a variation of an intensity I of incoming radiation in the respective field of view leads to a change of the respective post-processed sensor signal according to a desired mapping function $F_n(a_n,I)$, wherein the mapping functions $F_n()$ of all factory-balanced sensor elements are equal to each other and $a_n$ is a sensor element-individual factor; and a shading corrector implemented to change the sensor element-individual factors $a_n$ on the basis of a recording under current recording conditions generated by means of the camera arrangement with the sensor elements so that intensity differences of the recording are balanced across the common object plane.

According to another embodiment, a camera arrangement for image detection, including a plurality of radiation-sensitive sensor elements arranged to record a common object plane in offset fields of view, may have: a balancer implemented, for balancing the sensor elements, to post-process for each sensor element a sensor signal of the respective sensor elements n by means of balancing information determined in balancing and stored, so that a variation of an intensity I of incoming radiation in the respective field of view leads to a change of the respective post-processed sensor signal according to a desired mapping function $F_n(a_n I)$, wherein the mapping functions $F_n(\ )$ of all factory-balanced sensor elements are linear and equal to each other and $a_n$ is a sensor element-individual factor; and a shading corrector implemented, on the basis of post-processed sensor signals of the plurality of sensor elements, from a recording under current recording conditions, to weight the sensor element individual factors $a_n$ with a sensor element-individual scaling factor $s_n$, so that intensity differences of the recording are balanced across the common object plane.

According to another embodiment, an X-ray system for x-ray image detection may have: a radiation source; and a camera arrangement according to claim 1.

According to another embodiment, a camera arrangement for image detection including a plurality of radiation-sensitive sensor elements which are arranged to record a common object plane in offset fields of view may have: the first post-processor implemented to post-process sensor signals of the plurality of radiation-sensitive sensor elements by means of balancing information determined in balancing and stored, so that a variation of an intensity I of an incoming radiation in the respective field of view leads to a change of the respective post-processed sensor signal according to a desired mapping function $F_n(a_n I)$, wherein the mapping functions $F_n(\ )$ of all factory-balanced sensor elements are linear and equal to each other and $a_n$ is a sensor element-individual factor; and a second post-processor implemented to post-process the post-processed sensor signals by means of sensor element-individual factors $g_n$ determined under current recording conditions.

According to another embodiment, a method for balancing a camera arrangement for image detection, including a plurality of radiation-sensitive sensor elements arranged to record a common object plane in offset fields of view, may have the steps of: recording the object plane with an intensity distribution across the object plane by means of a camera arrangement; post-processing a sensor signal of the respective sensor element n for each sensor element n by means of balancing information determined in balancing and stored, so that a variation of an intensity I of incoming radiation in respective field of view leads to a change of the respective post-processed sensor signal according to a desired mapping function $F_n(a_n I)$, wherein the mapping functions $F_n(\ )$ of all factory-balanced sensor elements are equal to each other and $a_n$ is a sensor element-individual factor; and changing the sensor element-individual factors $a_n$ on the basis of a recording under current recording conditions executed by means of the camera arrangement with the factory-balanced sensor elements so that intensity differences of the recording are balanced across the common object plane.

According to another embodiment, a method for operating a camera arrangement for image detection, including a plurality of radiation-sensitive sensor elements, arranged to record a common object plane in offset fields of view, may have the steps of: post-processing sensor signals of the plurality of radiation-sensitive sensor elements by means of balancing information $f_n$ determined in balancing and stored, so that a variation of an intensity I of incoming radiation in the respective field of view leads to a change of the respective post-processed sensor signal according to a desired mapping function $F_n(a_n I)$, wherein the mapping functions $F_n(\ )$ of all factory-balanced sensor elements are linear and equal to each other and $a_n$ is a sensor element-individual factor; and post-processing the post-processed sensor signals by means of sensor element-individual factors determined under current recording conditions.

According to another embodiment, a computer program may have a program code for executing the above methods, wherein the program is executed on a computer.

According to another embodiment, a planar computer tomography or a robot computer tomography system may have the above camera arrangements.

Embodiments of the present invention provide a camera arrangement for image detection comprising a plurality of radiation-sensitive sensor elements which are arranged to record a common object plane in fields of vision offset to each other. The camera arrangement further includes a balancer implemented, for balancing the sensor elements to post-process for each sensor element a sensor signal of the respective sensor elements n by means of balancing information determined in factory-balancing and stored, so that a variation of an intensity I of an incoming radiation in the respective field of view leads to a change of the respective post-processed sensor signal according to a desired mapping function $F_n(a_n I)$ or $J_n(AW_n(I)-AW_n(I=0))$. The mapping functions $F_n(\ )$ of all factory-balanced sensor elements are equal to each other, wherein $a_n$ is a sensor-individual factor. Further, the camera arrangement includes a shading corrector implemented to change the sensor-individual factors $a_n$ on the basis of a recording generated by means of the camera arrangement with the sensor element so that intensity differences of the recording are balanced across the common object plane.

Embodiments of the invention are based on a division of balancing taking place with a camera arrangement. In a first initial step (factory-balancing), the basic performance of each pixel of the camera arrangement is factory-balanced to imprint for example a linear or exponential characteristic line onto each pixel. In a second step (shading correction) which may take in situ by means of a two point balancing (light/dark balancing) to be executed quickly, then simultaneously differences with respect to scaling, i.e. between individual output absolute values of the sensor signals at a certain intensity I and with respect to an inhomogeneous intensity distribution across the field of view of the camera arrangement are balanced. Across both calibration steps (factory-balancing, shading correction) the sensor signal to be output is changed by the respective balancing step or post-processing step while the basic connection between an intensity I (of radiation impinging upon the respective pixel) and the respective mapping functions $F_n(a_n I)$ or $G_n(I)$ is maintained. All in all, the described device or the described method provides the advantage by dividing balancing to reduce the effort for generating balancing recordings, e.g. after changing the x-ray parameters or after changing the position of the x-ray camera in the inhomogeneous radiation field.

According to further embodiments, the present invention provides an x-ray system for x-ray image detection with a radiation source and an above-described camera arrangement.

According to a further embodiment, the present invention provides a method for balancing a camera arrangement for image detection. Here, the camera comprises a plurality of radiation sensitive sensor elements which are arranged to record a common object plane in light fields offset to each other. The method comprises the step of recording the object plane with an intensity distribution across the object plane by means of the camera arrangement. Further, the method comprises the step of post-processing a sensor signal of the respective sensor element n for each sensor element n by means of factory-balancing determined and stored balancing information so that a variation of an intensity I of an incoming radiation in the respective field of view leads to a change of the respective post-processed sensor signal according to a desired mapping function $F_n(a_n I)$. The mapping functions $F_n()$ of all factory-balanced sensor elements are equal to each other, wherein $a_n$ is a sensor-individual factor. Further, the method includes a step of changing the sensor-individual factors $a_n$ on the basis of a recording made by means of the camera arrangement using the factory-balanced sensor element, so that intensity differences of the recording may be balanced across the common object plane.

BRIEF DESCRIPTION OF THE DRAWINGS

Embodiments of the present invention will be detailed subsequently referring to the appended drawings, in which:

FIG. 3b shows a table with exemplary camera signals according to the embodiment of FIG. 3a;

FIG. 4b shows a table with exemplary camera signals according to the embodiment of FIG. 4a.

DETAILED DESCRIPTION OF THE INVENTION

Figure 1:
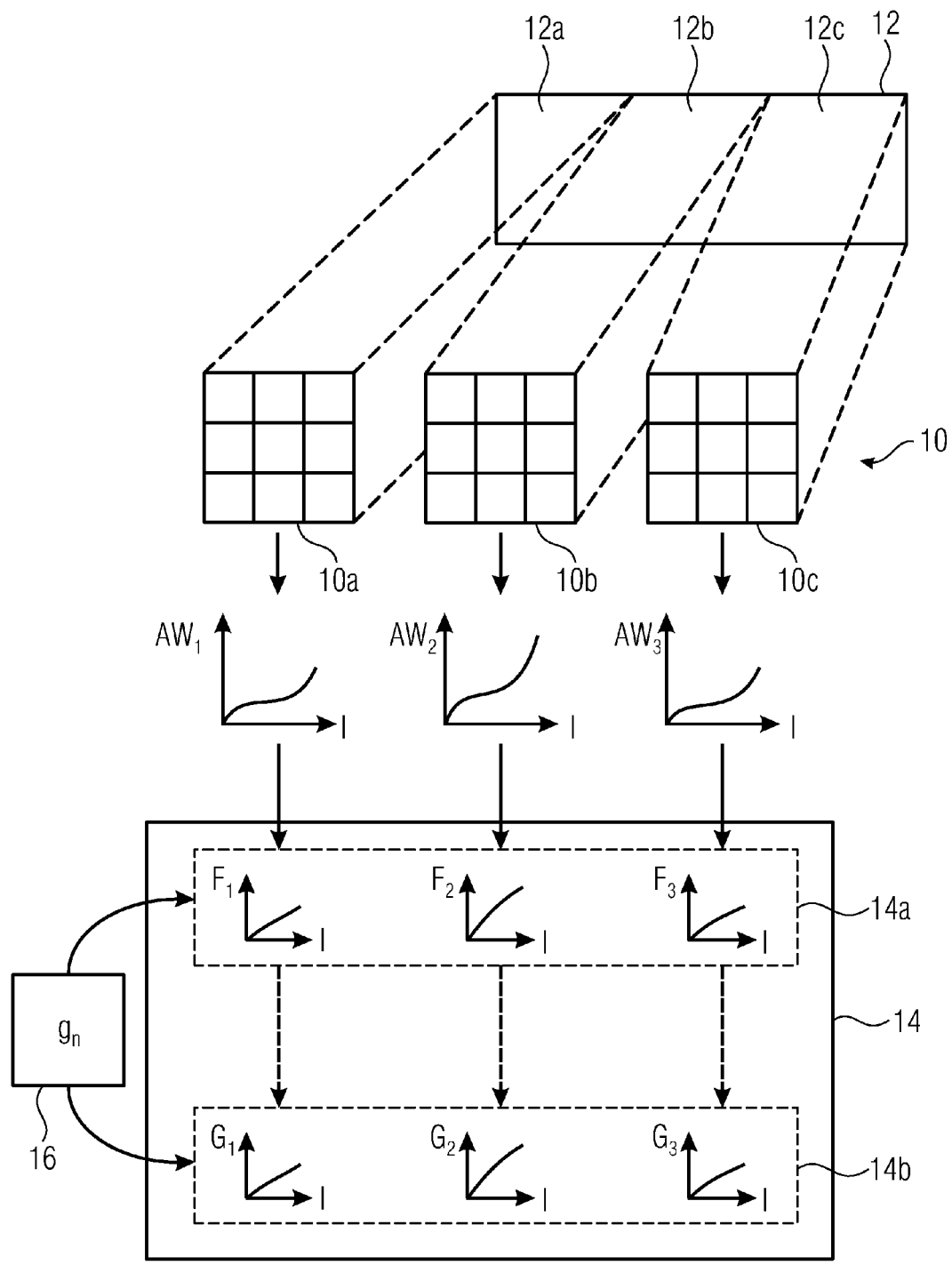
FIG. 1 shows a schematic illustration of a camera arrangement with a balancer and a shading corrector for the illustration of the principle of the divided signal processing according to one embodiment.

Before embodiments of the invention are explained in more detail in the following, it is noted that like elements or seemingly like elements are provided with the same reference numerals so that the description of the elements may be applied in a mutually interchangeable way.

FIG. 1 shows a camera arrangement 10 for image detection including a plurality of radiation-sensitive sensors elements, for example three sensor elements 10a, 10b and 10c. The three sensor elements 10a, 10b and 10c are arranged to record the common object plane 12, wherein each of the three sensor elements 10a, 10b and 10c is arranged to each record a section of the object plane 12 or one of the fields of view 12a, 12b and 12c of the object plane 12 offset to each other. The fields of view 12a, 12b and 12c are either overlapping, distributed and/or directly adjacent to each other so that the common object plane 12 is covered. Each of the sensor elements 10a, 10b and 10c, e.g. cameras, CCDs or pixels or a pixel array, outputs a sensor signal $AW_n(I)$ depending on an intensity I (dose [Gy]) of an incoming radiation in the respective field of view. These sensor signals $AW_1(I)$, $AW_2(I)$ and $AW_3(I)$ for the three sensor elements 10a, 10b and 10c are illustrated exemplarily in FIG. 1 depending on the radiation intensity I.

These sensor signals $AW_1(I)$, $AW_2(I)$ and $AW_3(I)$ depending on the intensity I are balanced by a balancer 14 which may comprise a first stage 14a and a second stage 14b, as it will be explained in more detail later, or post-processed by means of balancing information determined by factory-balancing, so that the sensor signals output by the balancer 14 correspond to a desired connection between the intensity I and the post-processed sensor signal. The balancer 14 and the sensor elements 10a, 10b and 10c are arranged in series so that the balancer 14 acquires the sensor signals $AW_1(I)$, $AW_2(I)$ and $AW_3(I)$ from the three sensor elements 10a, 10b and 10c. In addition to the balancer 14 a shading corrector 16 exists which is implemented to adapt the post-processing executed by the second stage 14b to an actual recording situation. In the following, the functioning of the balancer 14 and the shading corrector 16 and their cooperation is explained in detail.

The response signals $AW_1(I)$, $AW_2(I)$ and $AW_3(I)$ of the three sensor elements 10a, 10b and 10c, due to process fluctuations which are due to manufacturing each show a different performance with a variation of the radiation intensity I. Thus, for example, the response signals $AW_1(I)$ and $AW_2(I)$ may comprise non-linear performances while the response signal $AW_3(I)$ shows a virtually linear performance. Apart from that, also an average increase of $AW_1(I)$ and $AW_2(I)$, i.e. a sensitivity, may be different. In order to eliminate these effects the first stage 14a of the balancer 14 is implemented, for each sensor element 10a, 10b and 10c, to process the sensor signal $AW_1(I)$, $AW_2(I)$ and $AW_3(I)$ by means of factory-determined, sensor-individual balancing information $f_1$, $f_2$ and $f_3$ stored in the balancer 14, so that a variation of the intensity I of the incoming radiation leads, in the respective field of view 12, to a change of the respective factory-balanced signal according to a desired mapping function $F_1(a_1 I)$, $F_2(a_2 I)$ and $F_n(a_n I)$. The balancing information $f_1$, $f_2$ and $f_3$ is determined in factory-balancing so that the desired mapping functions $F_1()$, $F_2()$ and $F_3()$ of all sensor elements 10a, 10b and 10c balanced at the factory are equal to each other, i.e. $F_1=F_2=F_3$. The mapping functions $F_1()$, $F_2()$ and $F_3()$ output by the first stage 14a may for example be linear, and may alternatively however correspond to a different function, like e.g. a square, exponential or logarithmic function. In particular for very high dynamic ranges it may be sensible, instead of a linear characteristic line, to generate a logarithmic characteristic line, i.e. logarithmic functions $F_1()$, $F_2()$ and $F_3()$. It is further noted that the first stage 14a of the balancer 14 typically subtracts the temperature-dependent dark signal determined by means of a dark image from the current sensor signal $AW_n(I)$ in order to compensate temperature effects. This dark image is typically determined during the shading correction explained in the following (image shading correction or homogenization), i.e. under current recording conditions (e.g. sensor temperature, illumination period).

Thus, the sensor signals $F_1(a_1 I)$, $F_2(a_2 I)$ and $F_3(a_3 I)$ for the individual sensor elements 10a, 10b and 10c balanced at the factory are balanced in the first stage by the first post-processor 14a so that independent of the x-ray parameters or the position they at least show the same performance (like e.g. a linear performance or an exponential performance) or are even equal. It is to be noted here that the sensor-individual factors $a_1$, $a_2$ and $a_3$ may be different after factory-balancing among the sensor elements 10a, 10b and 10c, but do not have to be. For example for the case that the camera arrangement 10 comprises three matrix detectors having a plurality of pixels each, the sensor-individual factors for the pixels of one of the three matrix detectors are similar or equal. In particular, within one matrix detector, the above-mentioned similarities may be calculated (and for example are dependent on the distance of the respective pixel from the center pixel) so that it may be sufficient to determine one sensor individual factor for each matrix detector and to settle the same for each pixel with a pixel-individual factor which is determined by the position of the respective pixel within the matrix detector (e.g. center pixel=1.0 remaining pixel=1/distance to center pixel). Balancing at the factory leading to the balancing information $f_1$, $f_2$ and $f_3$ for example provides for uniformly illuminating the field of view 12, i.e. in consecutive recordings with a graded illumination intensity. If uniformity is not perfect now, as for example homogeneous illumination fields may be generated only very restrictedly, this possible irregularity is reflected in the sensor-individual factors $a_1$, $a_2$ and $a_3$. A 100% homogeneous radiation field or 100% equal $F(a_n I)$ are not absolutely imperative, as after the balancing at the factory at least each individual sensor element 10a, 10b and 10c of the camera arrangement 10 follows a desired mapping function $F_n(a_n I)$ even if they do not necessarily comprise the same slope or gradient. It is to be noted here that the sensor-individual factor $a_1$, $a_2$ and $a_3$ is introduced into the slope of the response of the factory-balanced sensor elements 10a, 10b and 10c, so that for example the mapping function is steeper when $a_n$ is greater or vice versa. Consequently, when in the balancing recordings a certain sensor element 10a is arranged in a less illuminated portion of the object plane 12 without the same being corrected separately, its sensor-individual factor $a_1$ is greater than the one of the other sensor elements 10b or 10c. To determine these sensor-individual factors $a_1$, $a_2$ and $a_3$, in factory-balancing for each sensor element 10a, 10b and 10c the response, i.e. the characteristic line of the output sensor values $AW_1(I)$, $AW_2(I)$ and $AW_3(I)$ is sampled for different intensities I so that the sensor values $AW_1(I)$, $AW_2(I)$ and $AW_3(I)$ may be balanced by the determined balancing information $f_1$, $f_2$ and $f_3$. Balancing information $f_1$, $f_2$ and $f_3$ determining these mapping functions $F_1(a_1 I)$, $F_2(a_2 I)$ and $F_3(a_3 I)$ are typically determined before the delivery of the camera arrangement 10 by means of factory-balancing, as briefly described above, and stored in the balancer 14 or provided as a separate "balancing" file.

When the intensity distribution is known in a non-homogeneous radiation field, by a subsequent correction of the balancing information $f_1$, $f_2$ and $f_3$ it may be achieved that the mapping functions F1(a1I), F2(a2I) and F3(a3I) balanced at the factory are equal with respect to their absolute values for each sensor element 10a, 10b and 10c with an impinging radiation of an intensity I. Thus, the balancing information $f_1$, $f_2$ and $f_3$ is typically selected so that the mapping functions $F_1(a_1 I)$, $F_2(a_2 I)$ and $F_3(a_3 I)$ are equal, i.e. $F_n(a_n I)=F_i(a_i I)$ with $a_n=a_i$ for all n≠i and all I, the values output by the balancer 14 or the first stage 14a of the balancer 14 may vary for each sensor element 10a, 10b and 10c. As illustrated below, the sensor-individual factors $a_n$ are anyway still to be set by the shading corrector 16. But even if actually with factory-balancing all sensor-individual factors $a_n$ ought to be equal, one possible reason for the variation may be that temperature differences of the individual sensor elements 10a, 10b and 10c or aging shifted their characteristic lines with respect to each other, which manifests itself by the sensor individual factors $a_1$, $a_2$ and $a_3$ and $a_n$ not being balanced. The latter balancing deficits are actually not severe or may be balanced by a high accuracy when balancing at the factory. What is more important is that frequently in the application of the camera arrangement 10 illumination varies laterally and thus has to be balanced anyway.

In order to in particular level the latter effect, the shading corrector 16 is implemented to change the sensor-individual factors $a_1$, $a_2$ and $a_3$ so that intensity differences of recordings in the application are balanced across the common object plane 12. Thus, the shading corrector 16 is communicatively coupled to the balancer 14 to adapt these sensor-individual factors $a_1$, $a_2$ and $a_3$ or the mapping functions $F_2(a_2 I)$ and $F_3(a_3 I)$ in homogenization. In case of a two-stage setup of the balancer 14, the shading corrector 16 may be arranged between the first stage 14a of the balancer 14 and the second stage 14b of the balancer 14, so that it sets the (homogenization) stage 14b so that the latter corrects the mapping functions $F_1(a_1 I)$, $F_2(a_2 I)$ and $F_3(a_3 I)$ of the first stage by means of shading information $g_1$, $g_2$, $g_3$. After shading correction, with the factory-balanced shading-corrected sensor signal output by the balancer 14, inhomogeneities of the radiation field are reduced or even eliminated.

The adaptation of the sensor-individual factors $a_1$, $a_2$ and $a_3$ executed by the shading corrector 16 or the determination of the changed sensor-individual factors $a'_1$, $a'_2$ and $a'_3$ is based on a recording of an intensity distribution (bright image) executed by means of a camera arrangement 10 or the sensor elements 10a, 10b and 10c. After shading correction, all sensor signals $AW_n(I)$ or sensor signals $F_n(a_n I)$ balanced at the factory are mapped by the balancer 14 to a shading-corrected mapping function $G_n(I)$. Information that may be used for changing to the sensor-individual factors $a'_1$, $a'_2$ and $a'_3$ are stored in the balancer 14, i.e. in addition to the mapping functions $F_1(\ )$, $F_2(\ )$ and $F_3(\ )$ for the second balancer 14b or in the form of shading-corrected mapping functions $G_1(a'_1 I)$, $G_2(a'_2 I)$ and $G_3(a'_3 I)$ by replacing the mapping functions $F_1(\ )$, $F_2(\ )$ and $F_3(\ )$ for the balancer 14. Thus, either an "shading-corrected balancing" file which includes the shading-corrected mapping functions G1(a'1I), G2(a'2I) and G3(a'3I) may be generated on the basis of the "balancing" file delivered by the factory or the original "balancing" file may be overwritten.

In this described method of two-stage balancing, so to speak a division of the balancing of the sensor elements 10a, 10b or 10c or the camera arrangement 10 which is usually executed in one step, is made into the steps of factory-balancing for generating comparable mapping functions $F_1(a_1 I)$, $F_2(a_2 I)$, $F_3(a_3 I)$ and $F_n(a_n I)$ and shading-correction for reducing or eliminating the inhomogeneity of the radiation field. The two-stage balancing reduces the balancing effort during the actual use of the camera arrangement 10, in particular by the fact that the more cost and time consuming factory-balancing may be executed initially, i.e. before delivery ex works, in service or when taking into operation the camera arrangement 10, while the shading correction which causes substantially less effort takes place in operation (or when changing the x-ray parameters or the position).

Figure 2:
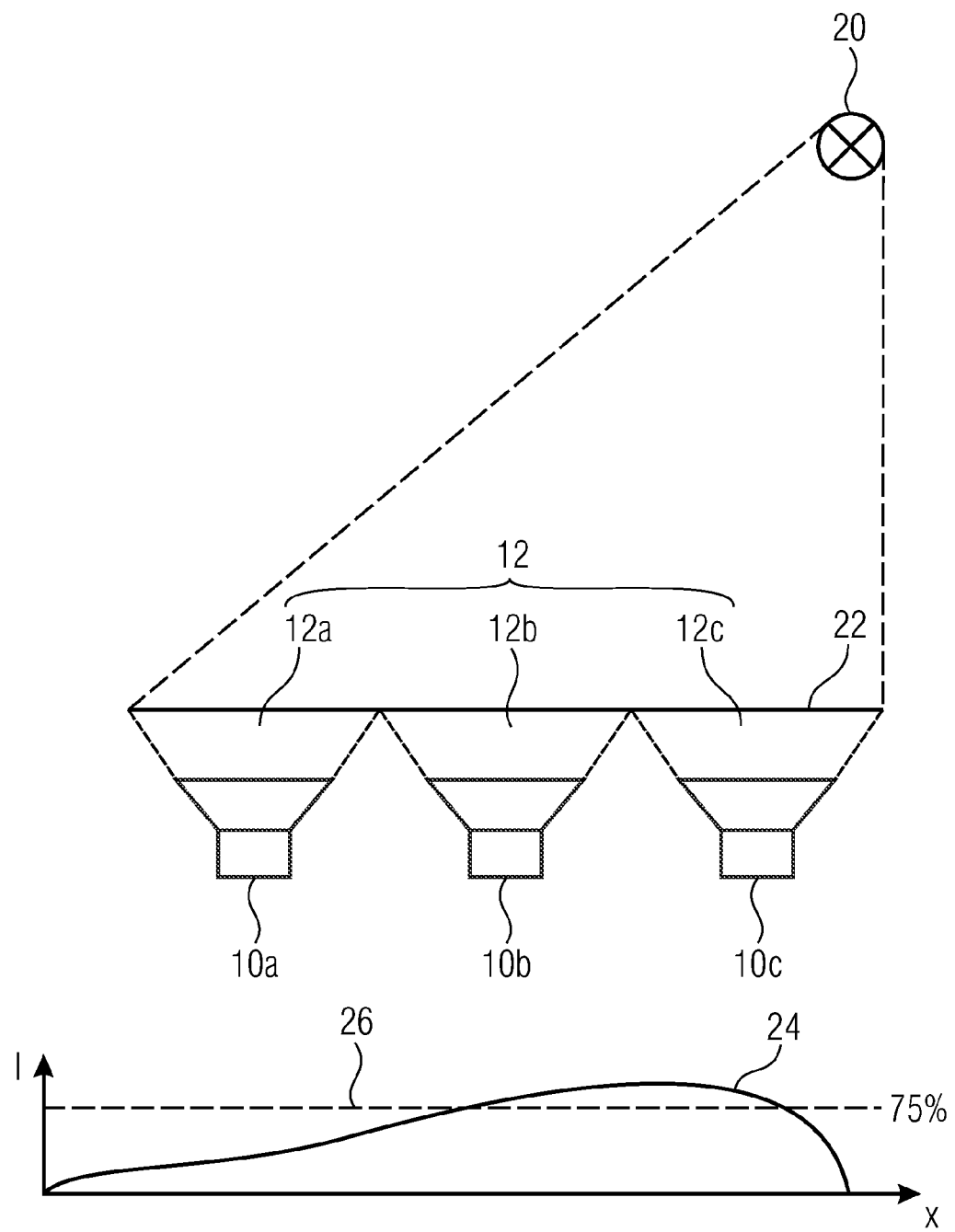
FIG. 2 shows a schematic illustration of an x-ray system arrangement for the illustration of intensity differences caused by the local position of the radiation source according to one embodiment.

With reference to FIG. 2, the background regarding inhomogeneity of the radiation source is explained and shading correcting is described by means of which the inhomogeneity effects of the radiation source may be eliminated. It is noted that when shading correcting methods are executed by the shading corrector 16, the balancer 14 or its balancing information is already set. As it was noted above, the latter, i.e. the shading correction information, is modified by the shading correction method or complemented by shading correction information.

FIG. 2 shows a radiation source 20 generating an intensity distribution of a radiation, like e.g. an ex-ray radiation, on a scintillator screen 22 so that an object may be x-rayed when it is arranged between the radiation source 20 and the scintillator screen 22. The scintillator screen 22 forms the object plane 12 with the fields of view 12a, 12b and 12c offset to each other which, as described in FIG. 1, are detected by the sensor elements 10a, 10b and 10c. Due to the fact that here exemplarily the radiation source 20 is further apart from the field of view 12a than from the field of view 12c, the radiation intensity I in the field of view 12a (detected by the sensor element 10a) is lower than the intensity I in the field of view 12c (detected by the sensor element 10c), as illustrated in the intensity diagram. Inhomogeneities may of course also occur in different ways. The offset arrangement of the radiation source 20 was here only used exemplarily.

The intensity diagram exemplarily illustrates the intensity distribution I depending on the position on the common object plane 12 or on the scintillator screen 22 using a graph 24. As it may be seen with respect to the graph 24, the intensity I is at maximum in the area in which the distance between the radiation source 20 and the scintillator screen 22 is minimal. If the balancer 14 were optionally balanced when recording the intensity distribution 24, i.e. if all $F_n$ and $a_n$ were be identical to each other, then by the sensor elements 10a to 10c the intensity course 24 in the image output by the balancer would be reproduced 1:1. But this is not necessarily desired, as the state illustrated in FIG. 2 without a screened object virtually represents an output state in which the image actually ought to constantly comprise the same (light) value. In this respect, the shading correction method is provided to either change the balancing information $f_n$ so that $a_n$ to $a'_n$ is varied so that the intensity course 24 is counteracted or in the two-stage case illustrated in FIG. 1 the second stage 14b of the balancer 14 is set so that it reforms the sensor signals of the first stage 14a factory-balanced by means of balancing information so that all in all in the balancer 14 mapping functions G1(a'1I), G2(a'2I) and G3(a'3I) are realized, which comprise the corresponding factors $a_n'$.

To generate a constant intensity (see graph 26) or an image with a constant intensity distribution when recording the intensity distribution I without a screened or x-rayed object across the complete common object plane 12, i.e. at the output of the balancer 14, $a_n$ are correspondingly corrected by means of the shading corrector 16. Here, for example, $a_n$ may be adapted so that the average value $\bar{a}_n$ is approximately equal to the average value $\bar{a}'_n$. Consequently, for example the factory-balanced sensor signals $F_1(a_1I)$ of the sensor elements 10a are corrected or adjusted upwards, while the factory-balanced sensor signals $F_3(a_3I)$ of the sensor elements 10c are corrected downwards, for example by setting $a_1$, greater than $a_1$ and setting $a_3$, smaller than $a_3$. In general this means that across all sensor elements 10a, 10b and 10c factory-balanced and shading corrected sensor signals $G_1(I)=F_1(a'_1I)$, $G_2(I)=F_2(a'_2I)$ and $G_3(I)=F_3(a'_3I)$ are set which correspond to a constant intensity distribution across the common object plane 12, as illustrated in graph 26. In other words, images recorded with the balancer 14 after shading correction with an illumination using the intensity distribution 24 are homogeneous, i.e. they have the same brightness across the complete image as it is illustrated at 26. It is noted that this applies independently of the fact using how much power the radiation source 20 is operated. As soon as the shading correction method has been executed, an image with the same brightness results. What is basically done, as will be described in the following, is that the shading corrector, with a varying intensity distribution 24 I(x), sees to the fact that independent of the set radiation power of the radiation source 20 in the intensities in the fields of view 12a to 12c of the sensor elements 10a to 10c comprise a fixed relationship to each other, like e.g. $b_n I_{radiationsource}$. The different $b_n$ correspond to the shape of the intensity distribution 24. $a_{n'}$ are now set so that $a'_n \times b_n = 1$.

By this it is realized that after the shading correction method each sensor element outputs 10a-10b $G(I_{radiationsource})=G_n(I_{radiationsource})$, i.e. the same for all.

In shading correction a change of the sensor-individual factors $a_1$, $a_2$ and $a_3$ into the sensor-individual factors $a'_1$, $a'_2$ and $a'_3$ is executed as described above. The step of changing the sensor-individual factors $a_n$ corresponds to a post-processing by means of shading correction information $g_n$ of the function $F_n(a_nI)$, so that in the function $F_n(a_nI)$ the sensor-individual factor $a_n$ is exchanged by a sensor-individual factor $a'_n$ so that the balancer 14 outputs $G_n=F_n(a'_nI)$. The determination of the changed sensor-individual factors $a'_1$, $a'_2$ and $a'_3$ may, for example, take place by a pixel-wise 2-point-balancing, wherein all pixels of the image sensors 10a, 10b and 10c are corrected without radiation to a defined dark value (for a reference intensity distribution) and with a switched-on radiation source 20 to a second defined light value (for an intensity distribution). This determined dark image or dark signal is, as described above, before the application or in the application of the balancing information $f_n$ in the first stage of the balancer 14, subtracted from the sensor signals $AW_n(I)$. For shading-correction typically a so-called light image is generated without an object using the factory setting (factory balancing information $f_n$) by the radiation source 20 which comprises a radiation intensity I which is selected so that the brightest pixel of the camera arrangement 10 has not yet reached saturation, i.e. is typically in range from 70 to 90% of the maximum signal. It is noted that the bright image contains no more dark signal due to the previous subtraction of the dark image. As long as the temperature and the illumination time do not change, alternatively for each test position also only the bright image may be newly recorded, as the dark image generally only changes with a temperature change or when changing the illumination time.

The regulation for determining the shading correction $G_n(a_nI)$ (homogenization) is $$G_n(a_nI)=H_n(J)=H_i(J)=H_j(J) \text{ and}$$

$$H_i(F(s_i \cdot a_i \cdot I_{p,i}))=H_j(F(s_j \cdot a_j \cdot I_{p,j})),$$

for scaling factors s and all combinations i, j (number index pixel in x- and y-directions).

$I_{p,i}$ designates the intensity irradiated with a certain parameter setting p in the pixel i, wherein the settable parameters for example are the acceleration voltage, the tube current, the integration time or the filter. The second index i is thus introduced, as in an inhomogeneous radiation field, the irradiated intensity I in a pixel i depends on the position in the detector. This condition is maintained even if the complete radiation field is scaled regarding its intensity with a scaling factor s, as far as no pixel is over-exposed. In the simplest case of $F(a_nI)$, the linear course with $a_n$=constant, the shading correction may be executed by each pixel being multiplied with an individual scaling factor $s_i$ or $s_j$ ($a_n'=s_i \cdot a_i$ and $a_n'=s_j \cdot a_j$) which is proportional to the inverse of this pixel of the balancing recording corrected by the factory setting. The proportionality factor has to be equal for the scaling factors of all pixels. In this case this also leads to a homogenization, when for generating the factory setting a radiation field of an unknown intensity distribution was used. If $F(a_nI)$ is defined differently, e.g. by a logarithmic course, a function has to be determined which fulfills the above regulation.

The condition for the in situ shading correction by means of the 2-point balancing is a preceding balancing by means of the first stage 14a of the balancer 14, so that all mapping functions $F_n(\ )$ are equal to each other, wherein the balancing information $f_n$ may be stored in the form of a lookup table and e.g. be delivered together with a camera arrangement 10. In the lookup table information may then be stored which for each entry (supporting location) maps a respective sensor signal interval to a (discrete) sensor value balanced at the factory. The number of supporting locations that may be used depends on the deviation of the course of $AW_i(I)$ with respect to $F(I)$. If the slope or inclination varies stronger in one of the two or in both courses, a larger number of supporting locations has to be used. If the two courses are very similar, a small number of supporting points or locations is sufficient. Supporting points or entries of directly subsequent sensor values accordingly correspond to an intensity interval determined by a top and a bottom threshold value and which has a constant length. As an alternative to storing by means of a lookup table, the balancing information $f_n$ may also be stored in a parametrical form, i.e., e.g. as coefficients of a polynomial. In both cases the camera arrangement 10 comprises a memory for storing the balancing information $f_n$ for each sensor element. As the lookup table or the polynomial depends on the individual sensor elements 10a, 10b and 10c, the same are individually determined for each sensor element 10a, 10b, 10c.

As already described above, the camera arrangement 10 for factory-balancing is exposed to a homogeneous radiation field whose intensity I is varied for balancing in order to generate a series of balancing recordings with a different intensity. One dark image each is printed from these balancing recordings wherein the dark image is recorded each with the same illumination time as the balancing recordings. Using this set of dark image-corrected balancing recordings it is possible to determine a generally valid set of balancing information $f_n$ in order to determine $F_n( )$. The regulation for gaining the balancing information $f_n$ is:

$$J_n(AW_n(I_k)-AW_n(I=0))=F(I_k) \text{ for all } k,$$

wherein $I_k$ covers the value range $I=0$ to $I_{max}$ for each pixel and $I_{max}$ is the intensity at which the n-th pixel provides the maximum response signal $AW_n( )$. In the present case of a radiography system it is also possible to replace the scintillator screen 22 for the initial balancing by a large-area homogeneous optical illumination whose brightness is increased in steps in order to acquire the requested balancing recordings. The spectrum (or the radiation characteristic) of the used optical illumination basically corresponds to that of the used scintillator screen 22.

Figure 3A:
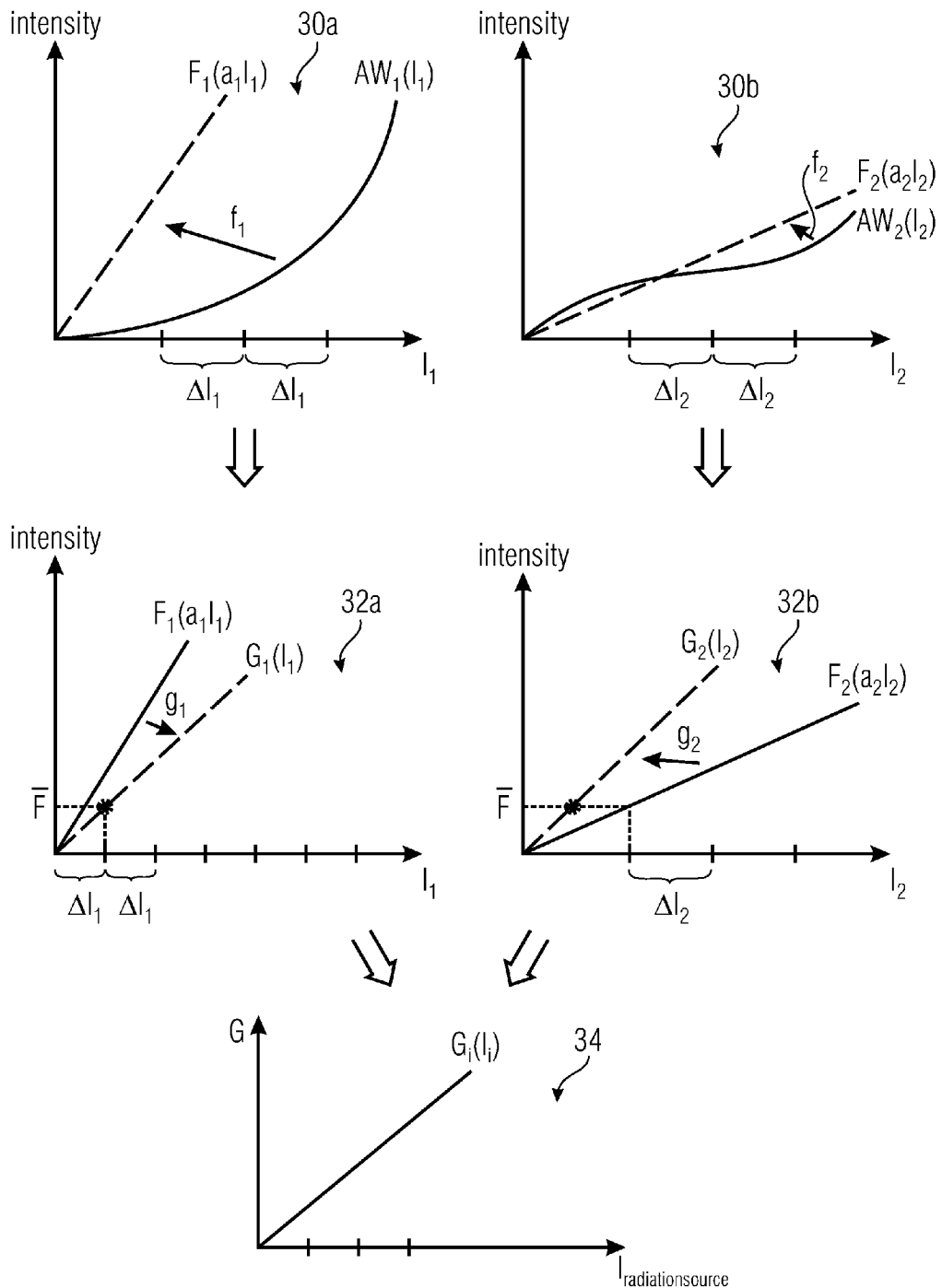
FIG. 3a shows schematic illustrations of camera signals for the illustration of the post-processing of the camera signals according to one embodiment (linear case)
Figure 4A:
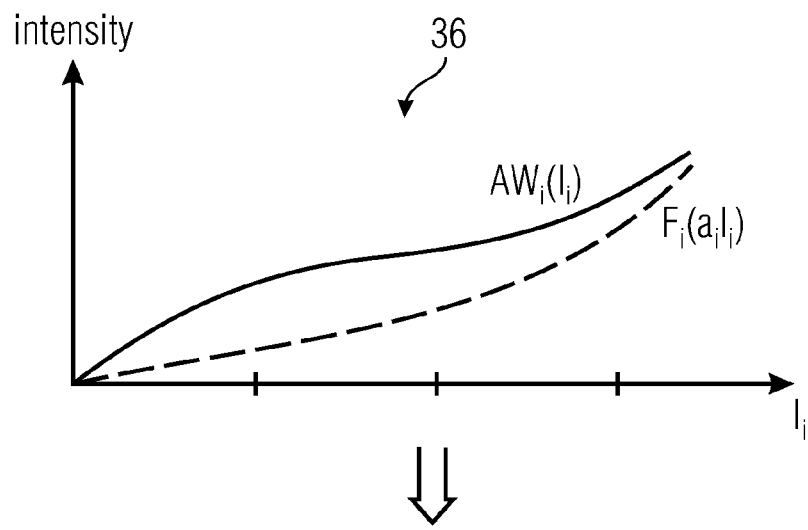
FIG. 4a shows schematic diagrams of camera signals for the illustration of the post-processing of the camera signals according to one embodiment (exponential case)
Figure 4A:
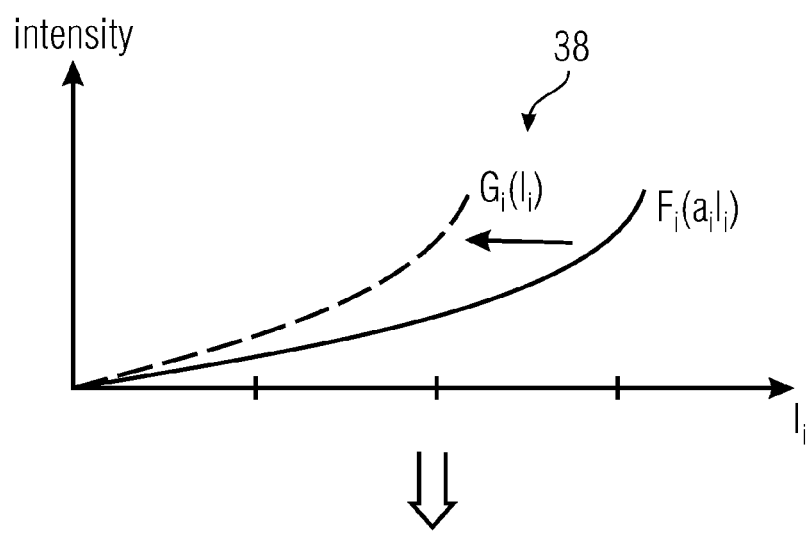
Figure 4A:
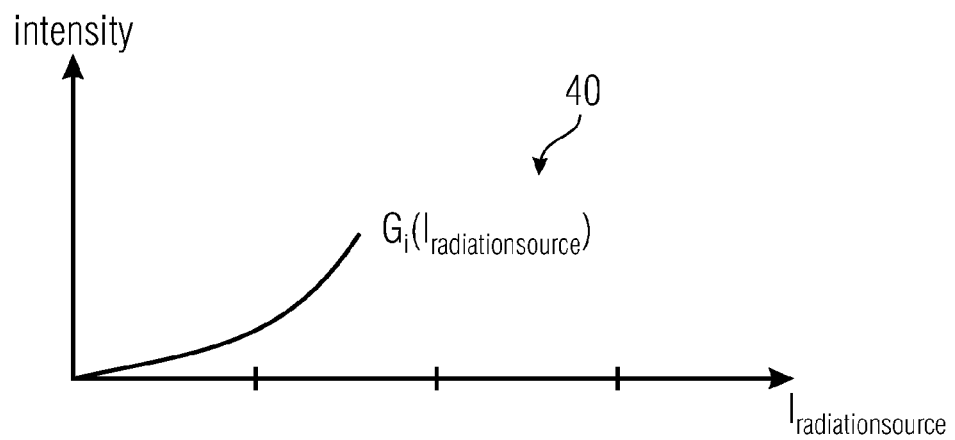

With respect to FIGS. 3 and 4, two embodiments with regard to balancing by means of the balancer and the shading corrector are explained in detail.

FIG. 3a shows the 2-stage balancing of a camera arrangement with respect to the example of two image sensors. In the following, the sensor signals of the two image sensors are explained as sensor signals of two pixels even if according to further embodiments the two sensor signals may belong to two CCDs or cameras. In FIG. 3a and the following FIGS. 3b and 3c it is assumed that the image sensor with the index 1 in the basic illumination state, i.e. the state in which after the shading correction method a homogeneous image is to be generated by the balancer 14, acquires the intensity $I_1$, while the sensor element with the index 2 acquires the intensity $I_2$, wherein $I_1:I_2=b_1:b_2$.

The diagram 30a illustrated in FIG. 3a illustrates the factory-balanced state (before the shading correction method), wherein the balancer reshapes or post-processes a dark image-corrected sensor signal $AW_1(I_1)$ (i.e. without offset) by means of balancing information $f_1$ for the first sensor element. Likewise, the diagram 30b shows the post-processing of a further dark image-corrected sensor signal $AW_2(I_2)$ by means of balancing information $f_2$ for the second sensor element.

The diagrams 30a and 30b each represent the sensor signals $AW_1(I_1)$ or $AW_2(I_2)$ depending on the intensity I ($I_1$ or $I_2$) The offset-corrected sensor signal $AW_1(I_1)$ output by the first sensor element exemplarily comprises an exponential course, while the second offset-corrected sensor signal $AW_2(I_2)$ comprises a wavy course. To imprint a similar characteristic upon these two intensity-dependent sensor signals $AW_1(I_1)$ or $AW_2(I_2)$ or even imprint the same the performance with the same absolute values $AW_1(I_1)$ or $AW_2(I_2)$ at the same intensity I, the sensor signals $AW_1(I_1)$ and $AW_2(I_2)$ for an intensity I are post-processed by the balancing information $f_1$ and $f_2$ determined (and stored) in balancing at the factory so that the balancer (e.g. using supporting points) maps the sensor signals $AW_1(I_1)$ or $AW_2(I_2)$ to balanced values, i.e. according to the mapping functions $F_1(a_1I_1)$ and $F_2(a_2I_2)$. These functions $F_1(a_1I_1)$ and $F_2(a_2I_2)$ are linear functions in the illustrated embodiments which may differ, however, with respect to their inclination. This effect may, as described above, be due to an inhomogeneity of the radiation field when balancing. Advantageously, $a_1$ and $a_2$ are linear or equal to each other.

Possible different slopes or inclinations $a_1$ or $a_2$ of the two functions $F_1(a_1I_1)$ and $F_2(a_2I_2)$ have no influence on the final result, as such signal differences are balanced by the shading correction. FIG. 3a now shows two different proceedings how the shading correction may be executed. A first possibility is that with the two-stage setup of the balancer 14 of FIG. 1 the first balancing stage 14a executes the mapping of $AW_n(I_n)$ to $F_n(a_nI_n)$. The second balancing stage 14b then modifies this output by means of the shading correction information $g_n$, i.e. the first balancing stage result, to all in all acquire the function $G_n(I)$. The second balancing stage 14b is set by the shading corrector 16 so that the same post-processes signals $F_1(a_1I_1)$ or $F_2(a_2I_2)$ so that they are mapped to $G_1(I_1)=F_1(a'_1I_1)$ or $G_2(I_2)=F_2(a'_2I_2)$. If the irregular illumination is considered, with respect to the radiation source power measured in $I_{radiationsource}$ all in all equal responses of the balancer 14 result. I.e., all $AW_n(I_n)$ are mapped to $G=G_n(I_{radiationsource})$. The shading information $g_n$ defines mapping functions $g_n$ which map the output values $f_n(a_nI_n)$ of the balancing stage 14a to $G_n(I_n)=F_n(a_n'I_n)$.

The bypass via shading information $g_i$ is not strictly necessary, however. It is rather possible to directly modify balancing information $f_n$ so that they map the sensor values $AW_n(I_n)$ to $G_n(I_n)$. This is also explained in more detail in the following.

With reference to FIG. 3b, a concrete embodiment of the shading correction of the sensor signals $AW_1(I_1)$ to $AW_4(I_4)$ is explained for four pixels. FIG. 3b shows a matrix for four pixels with five different illumination intensities between 0 W and 4 W, wherein for each pixel and illumination intensity the sensor signal $AW_n(I_n)$, the mapping function $F_n(a_nI_n)$ and the shading-corrected mapping function $G_n(I_n)$ are illustrated. Further, opposed to the matrix is a diagram of the illumination intensity regarding which it may it may be gathered that pixels 2 and 3 are illuminated more strongly than pixels 1 and 4. In other words, the following applies $I_1:I_2:I_3:I_4=1:2:2:1$.

The four pixels show a different performance when changing a radiation intensity in a range between 0 W and 4 W. The first pixel has a linear range between 1 W and 3 W (see $AW_1$) while the second pixel comprises a linear range between 2 W and 4 W (see $AW_2$). It is further noted that pixel 1 even with no radiation (0 W) outputs a signal $AW_1$ (0 W), so that the sensor signal $AW1(0 W)$ is offset-corrected before balancing. The third and fourth pixel also each comprise a linear range between 2 W and 4 W (see $AW_3$ and $AW_4$), wherein the linear ranges are each on a different level. In a comparison with the illumination intensity to the individual pixels it may be seen that pixel 2 as compared to pixel 4 outputs values which are to small while pixel 4 as compared to pixel 3 outputs values which are too high.

For balancing by $f_n$, the response signals $AW_1(I_1)$ to $AW_4(I_4)$ are mapped pixel-wise to a desired mapping function, i.e. to a linear mapping function, so that each pixel at 0 W outputs a balanced signal ($F_n(0\ W)$ with the value 0 and at 4 W a balanced signal $F_n(4\ W)$ with the value 4. Balancing was assumed so that $a_n$ is equal for all n. Insofar, all pixels 1 to 4 are balanced such that with the same irradiation intensity I they output the same balanced sensor signal $F_1(a_nI)$ to $F_4(a_nI)$. As not the same irradiation prevails for all pixels as it may be seen with respect to the intensity radiation diagram, $a_n$ are shading-corrected by the shading corrector 16. It may be seen that before the shading correction with the illumination of 2 W illustrated below, pixel 1 and 4 each output a balanced sensor signal $F_1(2\ W)$ or $F_4(2\ W)$ having the value 1, while pixels 2 and 3 each output a balanced sensor signal $F_2(2\ W)$ or $F_3(2\ W)$ with the value 2. In the present embodiment, by the shading correction the factory-balanced sensor signals $F_1()$ to $F_4()$ are shading-corrected to the average value $\bar{F}$ of all factory-balanced sensor signals $F_1()$ to $F_4()$. For the second and third pixel, for which no attenuation takes place between the detected irradiation intensity and illumination, this means that to the sensor values $F_2(2\ W)$ or $F_3(3\ W)$ the average value $\bar{G}=1.5$ is associated as a shading-corrected sensor value $G_2(2\ W)$ or $G_3(2\ W)$. For the pixels 1 and 4 which are illuminated with half the intensity, this means that the average value 1.5 is associated with the factory-balanced sensor signals $F_1(1\ W)$ or $F_4(1\ W)$ as shading-corrected sensor signals $G_1(1\ W)$ or $G_4(1\ W)$. The further shading-corrected sensor signals $G_1(0\ W, 2\ W, 3\ W, 4\ W)$ or $G_4(0\ W, 2\ W, 3\ W, 4\ W)$ are accordingly adapted by scaling or multiplication so that the basic performance or the linear performance is maintained. In the next step, the scales of the pixels 1 and 4 are shifted such that the linearity is maintained and that with the same irradiation intensity I but a different illumination pixels 1 to 4 still output the same shading-corrected sensor signals $G_1()$ to $G_4()$.

After in FIGS. 3a and 3b the case of a linear scale was discussed, with respect to FIGS. 4a and 4b an exponential case is discussed.

FIG. 4a shows the two-stage post-processing or balancing of a sensor signal of a pixel, so that the mapping function $G_1(a_1I)$ represents an exponential (or alternatively a logarithmic or square) function. In the diagram 36 illustrated in FIG. 4a, the offset-corrected sensor signal $AW_1(I)$ comprises an s-shaped course across the intensity I, wherein the sensor signal $AW_1(I)$ is mapped so that a balanced sensor signal $F_1()$ is output by the first post-processing stage, wherein the course across the intensity I is exponential. Analog to the process illustrated in FIG. 3a, in the first balancing (see diagram 36) the sensor signals $AW_n(I)$ are shading-corrected for further pixels or image sensors. In the second step illustrated in diagram 38 the factory-balanced sensor signals $F_1()$ are shading-corrected in the second balancing stage so that the shading-corrected mapping function $G_1()$ results. The shading-corrected mapping function $G_1()$ is the same for all sensor elements (see diagram 40: $G_n(I)$). The exponential performance of the sensor signal $F_1(a_1I)$ across the intensity I set in the first balancing stage is not influenced by the second balancing stage, so that the shading-corrected mapping function $G_1(a_1I)$ also comprises an exponential course even if the same may have a different scaling.

FIG. 4b shows a matrix of the sensor signals for four pixels with a different irradiation intensity between 0 W and 4 W according to FIG. 3b. With the illustrated matrix, the sensor signals or offset-corrected sensor signals $AW_1(I)$ to $AW_4(I)$ are identical to the sensor signals illustrated in FIG. 3b for all irradiation intensities.

In contrast to the embodiment of FIG. 3b, here the sensor signals are illustrated logarithmically so that the factory-balanced mapping functions $F_1(a_1I)$ to $F_4(a_4I)$ across the irradiation intensity I show a course according to the e-function. For each pixel 1 to 4, the balanced sensor signal $F_1()$ to $F_4()$ is mapped to the same values, like e.g. $e^0$ for 0 W irradiation intensity and $e^4$ for 4 W irradiation intensity. According to the embodiment of FIG. 3b, e.g. caused by the position of the radiation source, the illumination of the first and fourth pixel is less with respect to the second and third pixel, so that in shading correction the sensor signals $G_n(I)$ are mapped to a predetermined value, like e.g. the average value in the illumination (e.g. 2 W). As with the second and third pixel no attenuation of the irradiation intensity takes place, the shading-corrected sensor signals $G_2$ (2 W) and $G_3$ (3 W) for a corresponding intensity, here 2 W, are mapped to the average value $\bar{G}=5$. As with the illustrated illumination with 2 W onto the first and fourth pixel an irradiation intensity of 1 W (0.5×2 W) results, the corresponding shading-corrected sensor signals $G_1$ (1 W) and $G_4$ (1 W) are also mapped to the same average value. The scales of the pixels 2 and 3 are scaled according to the e-function, while the scales of pixels 1 and 4 are scaled and shifted, so that in the illustrated illumination each pixel comprises the same performance with respect to intensity changes and the same absolute values. As a result this means that the camera arrangement with respect to the currently present inhomogeneous radiation field is shading-corrected for varying intensities. If the camera arrangement is brought into a different inhomogeneous radiation field (for example by changing the x-ray source/x-ray detector distance), as above described only a 2-point balancing may be used as all pixels behave alike.

To get back to the example of above with respect to the robot computer tomography system, now using the new divided balancing device the number of balancing recordings determined in operation may be substantially reduced, e.g. to 101 or 501 (100 or 500 bright images plus one dark image). This corresponds to a time saving in balancing of approximately 90%.

Figure 5:
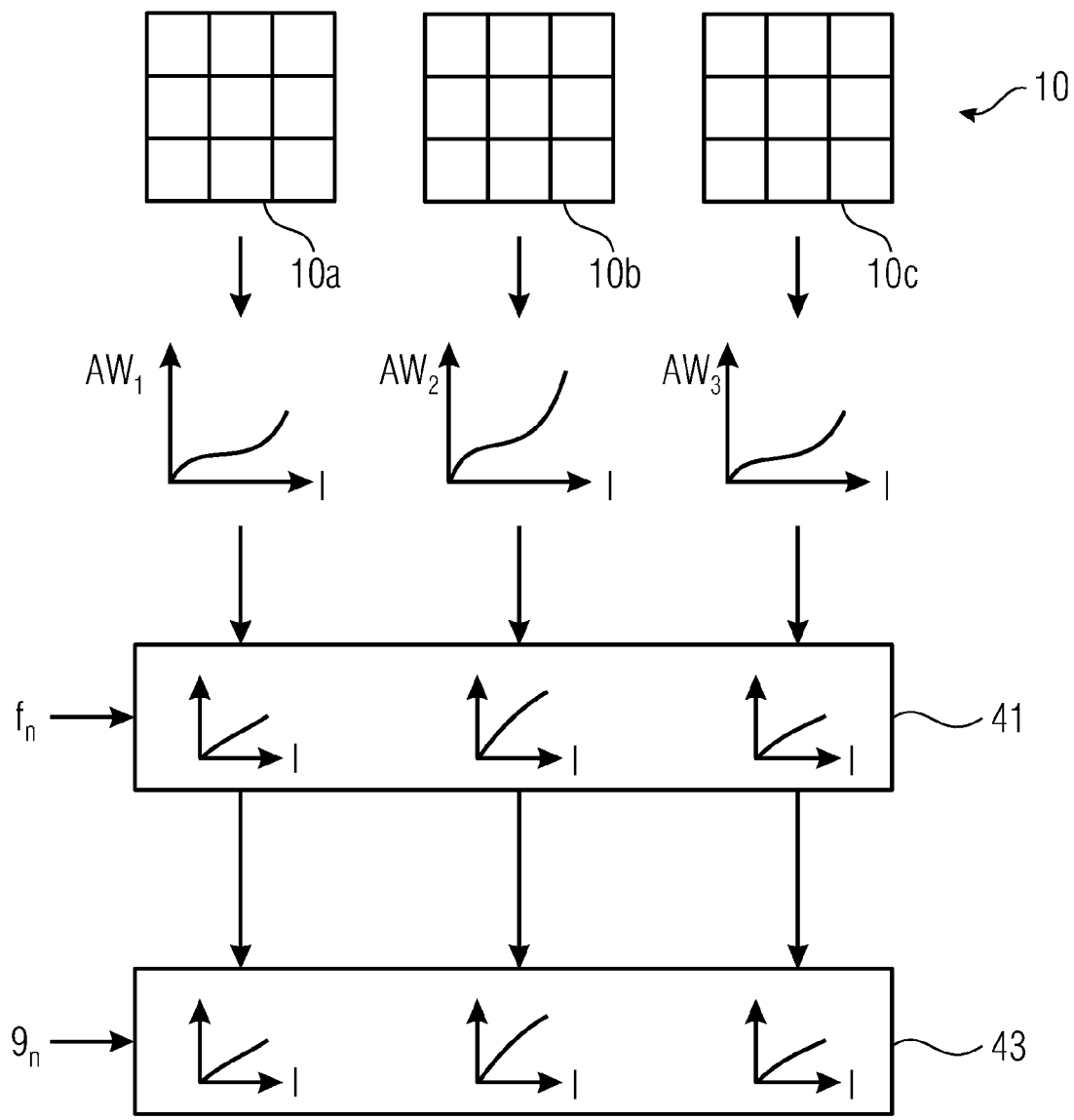
FIG. 5 shows a schematical illustration of a camera arrangement with a first post-processor and a second post-processor according to one embodiment.

FIG. 5 shows the camera arrangement 10 for image detection including the three sensor elements 10a, 10b and 10c, and a first post-processor 41 and a second post-processor 43. The three sensor elements 10a, 10b and 10c correspond to the sensor elements of FIG. 1 and output the sensor signals $AW_1(I)$, $AW_2(I)$ and $AW_3(I)$ to the first post-processor 41, e.g. a processor or CPU. The sensor signals post-processed by the first post-processor 41 are passed on to the second series-connected post-processor 43, e.g. a processor or CPU.

The first post-processor 41, e.g. a processor or CPU, processes the sensor signals after the offset-correction (subtraction of the dark signal $AW_n(I=0)$) according to the balancing information $f_1$, $f_2$ and $f_3$, which were determined in the initial balancing (see FIG. 1). As already mentioned above, these post-processed sensor signals show the same performance with advantageously the same absolute values at the same intensity I. I.e. the mapping functions $F_1()$, $F_2()$ and $F_3()$ are equal. As, however, depending on the respective measurement situation (positioning the radiation source) different illumination situations are set across the common object plane 12, the sensor signal which is post-processed in the first state is shading-corrected in a second stage with respect to the respective illumination situation. In this respect, the post-processor 43 is implemented to process the factory-balanced sensor signals by means of shading correction information $g_1$, $g_2$ and $g_3$, so that shading-corrected sensor signals corresponding to the shading-corrected mapping functions $G_1(a'_1 I)$, $G_2(a'_2 I)$ and $G_3(a'_3 I)$ are output. In case the mapping functions $F_1(\ )$, $F_2(\ )$ and $F_3(\ )$ are linear, this means the shading correction $g_1$, $g_2$ and $g_3$ represent a sensor-individual factor $g_1$, $g_2$ and $g_3$ by which the mapping functions $F_1(\ )$, $F_2(\ )$ and $F_3(\ )$ are multiplied so that their inclination is adapted individually to the respective illumination situation. This division is advantageous, as with each new illumination situation only shading correction information $g_1$, $g_2$ and $g_3$ are adapted and the originally determined balancing information $f_1$, $f_2$ and $f_3$ is not changed. As no change of the balancing information $f_1$, $f_2$ and $f_3$ takes place, rounding errors may not be exponentiated.

As already mentioned with reference to FIG. 2, the balancing information $f_1$, $f_2$ and $f_3$ and the shading correction information $g_1$, $g_2$ and $g_3$ are typically stored in a lookup table. In the following, the form of such a lookup table is explained in more detail, which as described above was determined when balancing by means of illumination intensities varied in steps.

In the lookup table for each pixel n or in the illustrated case for the pixel 1 and each intensity $I_1^{(j)}$ an interval of sensor signals $[AW_1^{(Intj)}(I_1^{(j)}); AW_1^{(Intj+1)}(I_1^{(j)})]$ is stored as a supporting point and associated with a certain mapping function $F_1(a_1 I_1^{(j)})$. For example, for the intensities $I_1^{(j)}$ to $I_1^{(j+3)}$ the following lookup table results for the balancing information $f_1$ of the pixel 1:

$I_1^{(j)} \to [AW_1^{(Intj)}(I_n^{(j)}); AW_1^{(Intj+1)}(I_1^{(j)})] [\to F_1(a_1 I_1^{(j)})$ $I_1^{(j+1)} \to [AW_1^{(Intj+1)}(I_n^{(j+1)}); AW_1^{(Intj+2)}(I_1^{(j+1)})$
$[\to F_1(a_1 I_1^{(j+1)})$ $I_1^{(j+2)} \to [AW_1^{(Intj+2)}(I_n^{(j+2)}); AW_1^{(Inti+3)}(I_1^{(j+2)})$
$[\to F_1(a_1 I_1^{(j+2)})$ $I_1^{(j+3)} \to [AW_1^{(Intj+3)}(I_n^{(j+3)}); AW_1^{(Intj+4)}(I_1^{(j+3)})$
$[\to F_1(a_1 I_1^{(j+3)})$ In the above illustrated table, so to speak each discrete intensity value $I_1^{(j)}$ is associated with one possible interval at sensor signals $[AW_1^{(Intj)}(I_1^{(j)})); AW_1^{(Intj+1)}(I_1^{(j)})[$, which is again mapped to a certain mapping function $F_1(a_1 I_1^{(j)})$. As an alternative, there are also further embodiments for such a lookup table, so that for example subsequent intervals of sensor signals $[AW_n^{(Intj)}(I_n^{(j)}); AW_n^{(Intj+1)}(I_n^{(j)})[$ relate to certain intensity ranges $I_n^{(j+1)}-I_n^{(j)}$ with each pixel n. In other words, this means that in lookup tables without a discrete intensity value all intensity ranges $I_n^{(j+1)}-I_n^{(j)}$ are constant, wherein each line of the lookup table relates to an intensity range. It is noted in general that the dependence of the mapping function $F_n(a_n I_n^{(j)})$ on the intensity I is not lost.

In the following, as an example, the adaption of the above-mentioned lookup table in shading correction is described. Here, with a standard illumination for each pixel n a value corresponding to the mapping function $F_n(a_n I_n^{(j)})$ is output on the basis of the above-described lookup table. In order to be able to output the same value for all pixels n with standard illumination, for example the output values are averaged according to the mapping functions $F_n(a_n I_n^{(j)})$, so that the average value $\overline{F_n(a_n I_n^{(j)})}$ results as a target value for all shading-corrected pixels. It is noted that also other values, like e.g. 75% to 90% of all values, may be defined as a target value. In a next step, for all pixels n those line indices $j_n$ are determined, possibly with the help of interpolation, so that the line indices $j_n$ each relate to the target value or average value $\overline{F_n(a_n I_n^{(j)})}$ for the corresponding pixel n. On the basis of the line index $j_n$ determined pixel-wise now a scaling or modification factor $a'_n$ is determined (pixel-wise) which maps the average value $\overline{F_n(a_n I_n^{(j)})}$ (or target value) to a value $G_n$ (standard illumination) which is the same for all pixels n for each individual pixel. The scaling factor $a'_n$ for each pixel n results from a random line index $j_{Soll}$ and the sensor-individual line index $j_n$, so that for the scaling factor $a'_n$ the following function results: $j_{Soll}/j_n$, wherein $j_{Soll}$ is the same for all pixels. Insofar, now with a standard illumination, a sensor signal is output by each pixel n which is associated with the entry in line $j_{Soll}$ in the shading-corrected lookup table and which is mapped for all pixels (independent of possible intensity inhomogeneities) on the basis of the shading-corrected lookup table to the value $G_n$ (standard illumination). With the mentioned scaling factor $a'_n$ now for each pixel all lookup values are shading-corrected. In the simplest case of a linear mapping function $F_n(a_n I_n)$ this process of shading correction corresponds to that of a multiplication with the scaling factor $a'_n$.

Further embodiments relate to an x-ray system having a radiation source and a camera arrangement comprising the above described aspects.

With respect to FIG. 3a it is noted that the shading correction of all mapping functions $G_n(I)$ to the average value $\overline{F}$ of all factory-balanced sensor signals $F_n(a_n I)$ may also be executed such that all shading-corrected mapping functions $G_n(\ )$ are mapped at a predetermined intensity to a predetermined value.

It is noted with respect to FIG. 4a, that the described proceeding is not limited to square functions but may also be applied with exponential, logarithmic or other mathematical functions.

Although some aspects were described in connection with a device or camera arrangement, it is obvious that these aspects also represent a description of the corresponding method for factory-balancing and shading-correction, so that a block or a member of a device may also be regarded as a corresponding method step or as a feature of a method step. Analog to that, aspects which were described in connection with or as a method step also represent a description of a corresponding block or detail or feature of a corresponding device. Some or all of the method steps may be executed by a hardware apparatus (or using a hardware apparatus) like e.g. a microprocessor, a programmable computer or an electronic circuit. In some embodiments some or several of the most important method steps may be executed by such an apparatus.

Depending on certain implementation requirements, embodiments of the invention may be implemented in hardware or in software. The implementation may be executed using a digital storage medium, for example a floppy disk, a DVD, a Blu-ray disc, a CD, an ROM, a PROM, an EPROM, an EEPROM or a FLASH memory, a hard disk or another magnetical or optical memory on which electronically readable control signals are stored which may cooperate or does cooperate with a programmable computer system such that the respective method is executed. Thus, the digital storage medium may be computer readable.

Some embodiments according to the invention thus include a data carrier comprising electronically readable control signals which are able to cooperate with a programmable computer system such that one of the methods described herein is executed.

In general, embodiments of the present invention may be implemented as a computer program product having a program code, wherein the program code is effective for executing one of the methods, when the computer program product is executed on a computer.

The program code may for example be stored on a machine readable carrier.

Other embodiments include the computer program for executing one of the methods described herein, wherein the computer program is stored on a machine readable carrier.

In other words, one embodiment of the inventive method is thus a computer program comprising a program code for executing one of the methods described herein, when the computer program is executed on the computer.

A further embodiment of the inventive method is thus a data carrier (or a digital storage medium or a computer readable medium) on which the computer program for executing one of the methods described herein is coded.

A further embodiment of the inventive method thus is a data stream or a sequence of signals which represents the computer program for executing one of the methods described herein. The data stream or the sequence of signals may for example be configured so as to be transferred via a data communication connection, for example via the internet.

A further embodiment includes a processing means, for example a computer or a programmable logics device which is configured or adapted so as to execute one of the methods described herein.

A further embodiment includes a computer on which the computer program for executing one of the methods described herein is installed.

A further embodiment according to the invention includes a device or a system which is implemented in order to transfer a computer program for executing at least one of the methods described herein to a receiver. The transmission may take place electronically or optically. The receiver may for example be a computer, a mobile device, a memory device or a similar device. The device or the system may, for example, be a file server for transferring the computer program to the receiver.

In some embodiments, a programmable logics device (for example a field programmable gate array, an FPGA) may be used to execute some or all functionalities of the methods described herein. In some embodiments, a field programmable gate array may cooperate with a microprocessor in order to execute one of the methods described herein. In general, in some embodiments the methods are executed by any hardware device. The same may be a universally useable hardware like a computer processor (CPU) or hardware which is specific for the method, like for example an ASIC.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

In the following, in summary the advantages of the above-described embodiments are described in other words.

The described method or the described device provides advantages when for a test problem (e.g. non-destructive tests of work pieces by means of x-ray) changing x-ray parameters, like e.g. x-ray tube voltage or current or illumination time or changing positions of the x-ray camera may be used with respect to the x-ray source.

One application example in this respect is the planar x-ray computer tomography. Here, a test object is screened from several different angles and from the gained projections the 3-dimensional setup of the test object is reconstructed. The proceedings are generally that for generating the different x-ray directions the relative position of x-ray source and x-ray tube are varied. Generally, 8 or 16 recordings may be used to be able to reconstruct the object 3-dimensionally with a sufficient accuracy. This means that for each of the 8 or 16 positions typically 5 to 20 balancing recordings have to be generated. As the balancing recordings generally do not have to be generated in the form of individual recordings but typically 8 or 16 or more individual recordings are averaged in order to reduce noise of the individual recordings, a substantial time effort results for generating the balancing recordings. Using the inventive balancing, when changing the recording position or other test parameters like tube voltage, only a 2-point balancing for each test position may be used.

In the following, the invention is again summarized in other words: the invention relates to a method (and the associated device) in two steps for balancing a camera. The first step of balancing is executed once or after a repair. The second step of balancing is executed after each change of operating parameters or operating conditions.

| 1st step | once | factory-balancing/factory setting F(aI) |
| --- | --- | --- |
| 2nd step | as needed | shading correction/homogenization |

In case of a linear course of F(aI) any intensity distribution of the radiation field may be used for determining the factory setting parameters. In this case it may only be achieved that the values corrected by the factory setting each increase linearly for all pixels with the irradiated intensity I. The proportionality factor by which the corrected value increases as a function of the irradiated intensity is generally different for all pixels then.

As the irradiated intensity generally varies across all pixels, it is advantageous for the shading correction (homogenization) of a recording not corrected by the factory setting to treat each individual pixel separately. I.e., after a change of the operating parameters and/or operating conditions a new set of balancing recordings is generated which characterizes the performance of the individual pixels in the given radiation field. By the factory settings at a known/homogeneous intensity distribution of the radiation field used for determining the factory setting, it is achieved that each pixel provides the same signal with the same irradiated intensity. It is thus possible to gain the information that may be used for the shading correction (homogenization) of a recording corrected by the factory setting from one single recording. When generating the recording for shading correction it is to be noted that no pixel is over-exposed and no object is located in the optical path. In general, the irradiated intensity is selected so that the lightest pixels are virtually completely illuminated. The advantage of this method is that the deviation of the response $AW_1(I)$ of all pixels is to be determined only once by F(i). Thus, it is possible, when changing operating parameters or operating conditions, to save the effort to again completely characterize all pixels.

DEFINITION OF MATHEMATICAL ELEMENTS

In the following, a short overview of the definitions of the substantial mathematical element is given:

I: dose rate integrated via illumination time.

$AW_n(I)$: uncorrected measurement signal of the pixel n.

$F_n(a_n I)$: corrected measurement signal as a function of the illumination intensity to be achieved by the factory setting. E.g. a linear response is to be acquired, but also any other course may be set (e.g. logarithmic, exponential, root-shaped, . . . ). It is to be noted that $F_n(a_n I)$ may also contain a fixed offset which is added to the resulting value of the function $F_n(a_nI)$. $F_n(a_nI)$ is advantageously identical for all pixels n.

$J_n(AW_n(I)-AW_n(I=0))$: measurement signal of the n-th pixel corrected by factory setting $H_n(J)=G_n(a_nI)$: shading-corrected (homogenized) signal of the n-th pixel K: count index of the supporting points for determining the factory setting.

The invention claimed is:

1. A camera arrangement for image detection comprising a plurality of radiation-sensitive sensor elements arranged in order to record a common object plane in offset fields of view, comprising:
   a balancer implemented, for balancing the sensor elements, to post-process for each sensor element a sensor signal of the respective sensor elements n by means of balancing information determined in balancing and stored, so that a variation of an intensity I of incoming radiation in the respective field of view leads to a change of the respective post-processed sensor signal according to a desired mapping function $F_n(a_nI)$, wherein the mapping functions $F_n(\ )$ of all factory-balanced sensor elements are equal to each other and $a_n$ is a sensor element-individual factor; and
   a shading corrector implemented to change the sensor element-individual factors $a_n$ on the basis of a recording under current recording conditions generated by means of the camera arrangement with the sensor elements so that intensity differences of the recording are balanced across the common object plane.

2. The camera arrangement according to claim 1, wherein the balancing information maps the sensor signals $AW_n(I)$ onto the mapping functions $F_n(a_nI)$ and are stored so that information on a relation between the mapping functions $F_n(a_nI)$ and the intensity I is maintained or generated from the balancing information.

3. The camera arrangement according to claim 1, wherein the balancing information is stored in the form of a lookup table which maps one sensor signal interval to a factory-balanced sensor value for each entry, wherein the entries of directly subsequent balanced sensor values comprise balance sensor values spaced apart by a constant intensity interval.

4. The camera arrangement according to claim 1, wherein the mapping functions $F_n(a_nI)$ for all factory-balanced sensor signals are linear, over-proportional, under-proportional, proportional or logarithmic functions.

5. The camera arrangement according to claim 1, wherein the camera arrangement comprises an external memory to the sensor elements in which the determined balancing information is stored for each sensor element.

6. The camera arrangement according to claim 1, wherein the shading corrector is implemented to post-process, for each sensor element the respective mapping function $F_n(a_nI)$ by means of shading correction information determined when recording, so that each sensor element performs according to the same shading-correcting mapping function $G_n=F_n(a'_nI)$ and intensity differences of the recording across the common object plane are balanced according to the shading-corrected mapping functions $G_n(I)$ wherein the shading-corrected mapping functions $G_n$ of all shading-corrected factory-balanced sensor elements are equal to each other and $a'_n$ is the changed sensor element-individual factor of the respective sensor element.

7. The camera arrangement according to claim 6, wherein the mapping function $F_n(a_nI)$ is a linear function with a constant increase $a_n$ and the shading corrector is implemented to post-process for each sensor element the respective linear mapping function $F_n(a_nI)$ by means of a multiplication with a sensor element-individual scaling factor $s_n$ so that each sensor element performs according to the same shading-corrected mapping function $G_n=F_n(s_na_nI)=F_n(a'_nI)$.

8. The camera arrangement according to claim 1, wherein the fields of view are distributed and/or adjacent and thus cover the common object plane, or wherein the fields of view are overlapping and thus cover the common object plane.

9. The camera arrangement according to claim 1, wherein each radiation sensitive sensor element is a pixel, a pixel array or a camera.

10. The camera arrangement according to claim 1, further comprising a signal combiner implemented to combine the sensor signals of the plurality of sensor elements into an overall image signal.

11. The camera arrangement according to claim 1, wherein the camera arrangement further comprises a plane scintillator screen in the common object plane.

12. A camera arrangement for image detection, comprising a plurality of radiation-sensitive sensor elements arranged to record a common object plane in offset fields of view, comprising:
   a balancer implemented, for balancing the sensor elements, to post-process for each sensor element a sensor signal of the respective sensor elements n by means of balancing information determined in balancing and stored, so that a variation of an intensity I of incoming radiation in the respective field of view leads to a change of the respective post-processed sensor signal according to a desired mapping function $F_n(a_nI)$, wherein the mapping functions $F_n(\ )$ of all factory-balanced sensor elements are linear and equal to each other and $a_n$ is a sensor element-individual factor; and
   a shading corrector implemented, on the basis of post-processed sensor signals of the plurality of sensor elements, from a recording under current recording conditions, to weight the sensor element individual factors $a_n$ with a sensor element-individual scaling factor $s_n$, so that intensity differences of the recording are balanced across the common object plane.

13. The camera arrangement according to claim 12, comprising a post-processor communicatively connected to the shading corrector and implemented to post-process the sensor signals post-processed by the balancer on the basis of the sensor element-individual scaling factors $s_n$.

14. An X-ray system for x-ray image detection, comprising:
   a radiation source; and
   a camera arrangement according to claim 1.

15. A camera arrangement for image detection comprising a plurality of radiation-sensitive sensor elements which are arranged to record a common object plane in offset fields of view, comprising:
   a first post-processor implemented to post-process sensor signals of the plurality of radiation-sensitive sensor elements by means of balancing information determined in balancing and stored, so that a variation of an intensity I of an incoming radiation in the respective field of view leads to a change of the respective post-processed sensor signal according to a desired mapping function $F_n(a_nI)$, wherein the mapping functions $F_n(\ )$ of all factory-balanced sensor elements are linear and equal to each other and $a_n$ is a sensor element-individual factor; and a second post-processor implemented to post-process the post-processed sensor signals by means of sensor element-individual factors $g_n$ determined under current recording conditions.

16. A method for balancing a camera arrangement for image detection, comprising a plurality of radiation-sensitive sensor elements arranged to record a common object plane in offset fields of view, comprising:
 recording the object plane with an intensity distribution across the object plane by means of a camera arrangement;
 post-processing a sensor signal of the respective sensor element n for each sensor element n by means of balancing information determined in balancing and stored, so that a variation of an intensity I of incoming radiation in respective field of view leads to a change of the respective post-processed sensor signal according to a desired mapping function $F_n(a_n I)$, wherein the mapping functions $F_n(\ )$ of all factory-balanced sensor elements are equal to each other and $a_n$ is a sensor element-individual factor; and
 changing the sensor element-individual factors $a_n$ on the basis of a recording under current recording conditions executed by means of the camera arrangement with the factory-balanced sensor elements so that intensity differences of the recording are balanced across the common object plane.

17. The method for balancing a camera arrangement according to claim 16, wherein the intensity distribution is selected such that the greatest post-processed sensor signal comprises a value in a range between 70% and 90% with respect to a maximum value of the respective balanced sensor signal.

18. The method for balancing a camera arrangement according to claim 16, further comprising recording a reference intensity distribution, wherein said generating of the shading correction information is executed on the basis of the two recordings of the intensity distribution and the reference intensity distribution.

19. The method for balancing a camera arrangement according to claim 16, wherein said generating of the shading correction information is executed such that each shading corrected mapping function $G_n = F_n(a'_n I)$ corresponds to a predetermined value or an average value of all factory-balanced sensor signals.

20. The method for balancing a camera arrangement according to claim 16, wherein said generating of the balancing information is executed for each sensor element; and
 wherein the balancing information $f_n$ is selected so that for each variation of the intensity I each mapping function $F_n(a_n I)$ corresponds to a predetermined value or an average value of all sensor signals.

21. The method for balancing a camera arrangement according to claim 16, further comprising initial balancing for determining the balancing information by means of a plurality of radiation fields varying with respect to intensity I which are generated by means of a planar radiation source instead of a scintillator screen,
 wherein the balancing information $f_n$ is selected so that each balanced sensor signal, with a constant variation of the intensity I, changes according to a linear, proportional, over-proportional, under-proportional or logarithmic mapping function.

22. A method for operating a camera arrangement for image detection, comprising a plurality of radiation-sensitive sensor elements, arranged to record a common object plane in offset fields of view, comprising:
 post-processing sensor signals of the plurality of radiation-sensitive sensor elements by means of balancing information $f_n$ determined in balancing and stored, so that a variation of an intensity I of incoming radiation in the respective field of view leads to a change of the respective post-processed sensor signal according to a desired mapping function $F_n(a_n I)$, wherein the mapping functions $F_n(\ )$ of all factory-balanced sensor elements are linear and equal to each other and $a_n$ is a sensor element-individual factor; and
 post-processing the post-processed sensor signals by means of sensor element-individual factors determined under current recording conditions.

23. The method for operating a camera arrangement according to claim 22, further comprising a method of balancing according to claim 16 before said post-processing of the post-processed sensor signals.

24. A computer program comprising a program code for executing the method according to claim 16, wherein the program is executed on a computer.

25. A computer program comprising a program code for executing the method according to claim 23, wherein the program is executed on a computer.

26. A planar computer tomography or a robot computer tomography system comprising the camera arrangement according to claim 1.

27. A planar computer tomography or a robot computer tomography system comprising the camera arrangement according to claim 12.

* * * * *